United States Patent
Loomba et al.

(10) Patent No.: US 10,422,786 B2
(45) Date of Patent: Sep. 24, 2019

(54) DIFFERENTIAL DIAGNOSIS OF LIVER DISEASE

(71) Applicant: The Regents of the University of California, Oakland, CA (US)

(72) Inventors: Rohit Loomba, San Diego, CA (US); Oswald Quehenberger, San Diego, CA (US); Aaron Armando, San Diego, CA (US); Edward A. Dennis, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 252 days.

(21) Appl. No.: 15/100,621

(22) PCT Filed: Dec. 9, 2014

(86) PCT No.: PCT/US2014/069389
§ 371 (c)(1),
(2) Date: May 31, 2016

(87) PCT Pub. No.: WO2015/089102
PCT Pub. Date: Jun. 18, 2015

(65) Prior Publication Data
US 2016/0305925 A1    Oct. 20, 2016

Related U.S. Application Data

(60) Provisional application No. 61/914,345, filed on Dec. 10, 2013.

(51) Int. Cl.
| | |
|---|---|
| *G01N 33/487* | (2006.01) |
| *G01N 30/72* | (2006.01) |
| *G01N 33/92* | (2006.01) |
| *G01N 33/88* | (2006.01) |
| *G16B 20/00* | (2019.01) |

(52) U.S. Cl.
CPC ....... *G01N 33/487* (2013.01); *G01N 30/7233* (2013.01); *G01N 33/88* (2013.01); *G01N 33/92* (2013.01); *G16B 20/00* (2019.02); *G01N 2800/085* (2013.01); *Y02A 90/24* (2018.01); *Y02A 90/26* (2018.01)

(58) Field of Classification Search
CPC .......... G06F 19/18; G06F 19/30; G06F 19/34; G16H 50/30; G01N 2800/085; G01N 2800/08; G01N 33/92
See application file for complete search history.

(56) References Cited

U.S. PATENT DOCUMENTS

| | | | |
|---|---|---|---|
| 5,753,702 A | 5/1998 | Bednar et al. | |
| 2010/0233724 A1* | 9/2010 | Watkins ................. | G01N 33/92 435/7.1 |
| 2013/0056630 A1 | 3/2013 | Feldstein et al. | |

FOREIGN PATENT DOCUMENTS

| | | |
|---|---|---|
| JP | 2010500566 | 1/2010 |
| WO | 2011/140093 A2 | 11/2011 |
| WO | 2012000770 A1 | 1/2012 |
| WO | 2012049874 | 2/2014 |

OTHER PUBLICATIONS

Ciccimaro, Eugene et al. "Stable-isotope dilution LC-MS for quantitative biomarker analysis." Bioanalysis (2010) 2 311-341. (Year: 2010).*
Mandrekar, Jayawant N. "Receiver operating characteristic curve in diagnostic test assessment." Journal of Thoracic Oncology (2010) 5 1315--1316. (Year: 2010).*
O'Halloran, Sean et al. "Evaluation of a deuterium labeled internal standard for the measurement of sirolimus by high-throughput HPLC electrospray ionization tandem mass spectrometry." Clinical Chemistry (2008) 54 1396-1389. (Year: 2008).*
Caruso, John L. et al. "Determination of indole-3-acetic acid in Douglas fur using a deuterated analog and selected ion monitoring." Plant Physiology (1978) 62 841-845. (Year: 1978).*
Gundlach, Bjorn, Supplementary Partial European Search Report, European Patent Office, Application No. 14870547.8, dated Jul. 7, 2017.
Loomba, Rohit et al., "Polyunsaturated fatty acid metabolites as novel lipidomic biomarkers for noninvasive diagnosis of nonalcoholic steatohepatitis", Journal of Lipid Research, Jan. 1, 2015, pp. 185-192.
Puri, Puneet et al., "The plasma lipidomic signature of nonalcoholic steatohepatitis", Hepatology, vol. 50, No. 6, Aug. 10, 2009, pp. 1827-1838.
Moon, Kihwan, International Preliminary Report on Patentability and Written Opinion, PCT/US2014/069389, The International Bureau of WIPO, dated Jun. 23, 2016.
Young, Lee W., Written Opinion on the International Searching Authority, PCT/US2014/069389, United States Patent & Trademark Office, dated Jan. 29, 2015.
Kusakawa, Takashi, Patent Application No. 2016-537504, Office Action, Japanese Patent Office, dated Aug. 28, 2018.

* cited by examiner (Continued)

*Primary Examiner* — Christopher Adam Hixson
(74) *Attorney, Agent, or Firm* — Gavrilovich, Dodd & Lindsey LLP

(57) ABSTRACT

The present invention relates to the substantially non-invasive diagnosis of liver disease, especially to enable intervention in the progression of such disease at an early stage. This invention further relates to the use of plasma biomarkers to differentiate nonalcoholic steatohepatitis (NASH) from nonalcoholic fatty liver (NAFL) and non-nonalcoholic fatty liver disease (NAFLD), and normal controls. Specifically, the invention relates to the use of free eicosanoids and other polyunsaturated fatty acid (PUFA) metabolite levels in plasma to differentiate NASH from NAFL and non-NAFLD normal controls.

17 Claims, 5 Drawing Sheets

Table 1. Baseline demographic, clinical, biochemical and histologic characteristics of the patients in the study population

| | Controls n=10 | NAFL n=10 | NASH n=9 | Control vs. NAFL P-values | NAFL vs. NASH P-values |
|---|---|---|---|---|---|
| Age | 31.8 ± 15.66 | 48.90 ± 14.03 | 45.89 ± 12.94 | 0.019 | 0.633 |
| Sex | 40% male | 44% male | 40% male | | |
| BMI | 24.73 ± 4.17 | 29.49 ± 5.39 | 29.59 ± 5.01 | 0.041 | 0.966 |
| Laboratory data | | | | | |
| Platelet | 240500 ± 48808.58 | 264900 ± 53371.76 | 244888.89 ± 52312.63 | 0.300 | 0.400 |
| WBC | 7.05 ± 1.90 | 7.18 ± 2.28 | 5.96 ± 0.87 | 0.892 | 0.101 |
| Alk P | 71.9 ± 23.65 | 85.70 ± 40.42 | 78.78 ± 18.19 | 0.367 | 0.638 |
| ALT | 16.7 ± 8.51 | 61.10 ± 39.73 | 104.33 ± 61.79 | 0.006 | 0.053 |
| AST | 23.1 ± 8.71 | 35.00 ± 12.53 | 66.33 ± 32.69 | 0.025 | 0.013 |
| D Bili | 0.12 ± 0.04 | 0.12 ± 0.04 | 0.12 ± 0.04 | 1.000 | 0.628 |
| T Bili | 0.49 ± 0.30 | 0.53 ± 0.21 | 0.56 ± 0.25 | 0.732 | 0.763 |
| GGT | 18.8 ± 19.52 | 46.20 ± 24.03 | 72.89 ± 38.47 | 0.012 | 0.067 |
| Glucose | 88.7 ± 5.93 | 99.00 ± 13.41 | 97.11 ± 8.68 | 0.046 | 0.612 |
| Hba1c | 5.6 ± 0.30 | 5.79 ± 0.82 | 5.84 ± 0.45 | 0.505 | 0.947 |
| Insulin | 8.7 ± 4.35 | 13.64 ± 6.23 | 14.78 ± 10.31 | 0.003 | 0.608 |
| PT | 10.98 ± 0.58 | 10.59 ± 1.33 | 10.77 ± 0.80 | 0.411 | 0.657 |
| Chol | 172.9 ± 21.46 | 196.60 ± 33.20 | 229.67 ± 28.97 | 0.077 | 0.050 |
| TG | 87.5 ± 41.70 | 124.80 ± 52.37 | 221.22 ± 108.43 | 0.096 | 0.034 |
| HDL | 58.1 ± 12.38 | 55.00 ± 18.34 | 55.44 ± 24.78 | 0.664 | 0.947 |
| LDL | 97.6 ± 18.40 | 116.50 ± 129.00 | 129.00 ± 26.88 | 0.083 | 0.294 |
| Liver Histology | | | | | |
| Steatosis | | 0.75 ± 0.5 | 2.33 ± 0.82 | | 0.005 |
| Fibrosis | | 0 ± 0 | 1.60 ± 0.89 | | 0.016 |
| NAS | | 1.75 ± 0.5 | 6.33 ± 1.03 | | 0.0001 |
| Hep. Balloon. | | 0 ± 0 | 1.50 ± 0.84 | | 0.007 |
| Lob. Infl. | | 1 ± 0 | 2.17 ± 0.41 | | 0.001 |
| Portal Infl. | | 0.5 ± 0.55 | 0.17 ± 0.41 | | 0.262 |

The p-values in bold are statistically significant (p ≤ 0.05).
Differences between groups evaluated with t-test.
BMI, Body Mass Index; AST, Aspartate Aminotransferase; ALT, Alanine Aminotransferase; Hgb A1C, hemoglobin A1C; LDL, Low-Density Lipoprotein; HDL, High-Density Lipoprotein; FFA, Free Fatty Acids; CRP, C-Reactive Protein; ALK Phos, Alkaline Phosphatase; GGT, Gamma-Glutamyl Transferase; HOMA, homeo-static model assessment; NAS, NAFLD Activity Score.

FIG. 3

Table 2. Eicosanoid metabolites in normal controls vs. non-alcoholic fatty liver vs. non-alcoholic steatohepatitis

| | Controls n=10 | NAFL n=10 | NASH n=9 | Control vs. NAFL p-values† | Control vs. NASH p-values† | NAFL vs. NASH p-values† | Compare all groups p-values‡ |
|---|---|---|---|---|---|---|---|
| Arachidonic Acid derived Metabolites (Units = pmol/ml) | | | | | | | |
| TxB2 | 0.23 ± 0.22 | 4.53 ± 8.52 | 5.47 ± 9.86 | 0.1452 | 0.1498 | 0.8261 | 0.2704 |
| 12-HHTrE | 1.06 ± 0.78 | 9.06 ± 16.00 | 23.07 ± 37.70 | 0.1485 | 0.1181 | 0.3242 | 0.1291 |
| PGE2 | 0.05 ± 0.06 | 0.05 ± 0.07 | 14.63 ± 0.12 | 0.9899 | 0.0437 | 0.0485 | 0.0408 |
| dhk PGD2 | 0.25 ± 0.16 | 0.29 ± 0.11 | 0.72 ± 0.27 | 0.4895 | 0.0002 | 0.0011 | <.0001 |
| 11-HETE | 0.22 ± 0.15 | 0.63 ± 0.62 | 0.75 ± 0.83 | 0.0681 | 0.0830 | 0.7134 | 0.1279 |
| 5-HETE | 1.04 ± 0.47 | 3.06 ± 3.65 | 1.85 ± 0.87 | 0.1156 | 0.0211 | 0.3300 | 0.1427 |
| 12-HETE | 5.47 ± 4.04 | 14.15 ± 14.04 | 13.42 ± 14.77 | 0.0883 | 0.1521 | 0.9141 | 0.2167 |
| Tetranor 12-HETE | 0.24 ± 0.11 | 0.25 ± 0.23 | 0.42 ± 0.20 | 0.8992 | 0.0196 | 0.0956 | 0.0714 |
| 15-HETE | 1.32 ± 0.35 | 2.08 ± 0.63 | 1.03 ± 0.53 | 0.0036 | 0.1684 | 0.0011 | 0.0004 |
| 5,6-diHETrE | 0.33 ± 0.09 | 0.53 ± 0.19 | 1.25 ± 1.28 | 0.0109 | 0.0521 | 0.1126 | 0.0180 |
| 11,12-diHETrE | 0.34 ± 0.18 | 0.41 ± 0.13 | 1.11 ± 0.31 | 0.2949 | <.0001 | <.0001 | <.0001 |
| 14,15-diHETrE | 0.95 ± 0.31 | 1.14 ± 0.30 | 1.64 ± 0.45 | 0.1847 | 0.0011 | 0.0101 | 0.0009 |
| 20-COOH AA | 7.41 ± 2.57 | 10.13 ± 3.45 | 38.94 ± 42.14 | 0.0607 | 0.0552 | 0.0747 | 0.0131 |
| Alternative Substrate Derived Metabolites (Units = pmol/ml) | | | | | | | |
| 13-HODE | 13.27 ± 12.07 | 10.18 ± 5.24 | 12.41 ± 8.80 | 0.4721 | 0.8529 | 0.5059 | 0.7415 |
| 9-HODE | 7.03 ± 6.14 | 6.25 ± 3.80 | 8.82 ± 6.51 | 0.7384 | 0.5444 | 0.3018 | 0.5984 |
| 9-oxoODE | 1.59 ± 1.19 | 1.40 ± 2.00 | 4.60 ± 4.60 | 0.7955 | 0.0887 | 0.0801 | 0.0420 |
| 9,10 EpOME | 4.08 ± 2.06 | 3.72 ± 2.78 | 3.73 ± 2.57 | 0.7448 | 0.7458 | 0.9928 | 0.9344 |
| 9,10 diHOME | 6.67 ± 6.00 | 3.14 ± 1.27 | 4.70 ± 2.57 | 0.0991 | 0.3611 | 0.1268 | 0.1455 |
| 12,13 EpOME | 1.89 ± 1.53 | 1.39 ± 1.63 | 5.64 ± 5.72 | 0.4936 | 0.0882 | 0.0592 | 0.2044 |
| 12,13 diHOME | 5.56 ± 2.55 | 3.59 ± 1.36 | 4.65 ± 2.07 | 0.0446 | 0.4103 | 0.1976 | 0.1187 |
| 9-HOTrE | 0.35 ± 0.47 | 0.25 ± 0.19 | 0.37 ± 0.22 | 0.5438 | 0.8789 | 0.1520 | 0.6624 |
| 15-HETrE | -- | -- | 0.04 ± 0.06 | -- | -- | -- | -- |
| 12-HEPE | 0.40 ± 0.37 | 1.40 ± 2.61 | 1.16 ± 0.90 | 0.2618 | 0.0391 | 0.7909 | 0.3771 |
| 14 HDoHE | 2.81 ± 2.21 | 5.71 ± 8.35 | 3.14 ± 2.70 | 0.3125 | 0.7725 | 0.3765 | 0.4233 |
| 16 HDoHE | 0.01 ± 0.02 | 0.11 ± 0.14 | 0.18 ± 0.16 | 0.0542 | 0.0139 | 0.3312 | 0.0201 |
| 19,20 DiHDPA | 1.71 ± 0.52 | 2.39 ± 1.72 | 3.14 ± 1.28 | 0.2558 | 0.0101 | 0.2996 | 0.0672 |

NAFL, non-alcoholic fatty liver disease; NASH, non-alcoholic steatohepatitis;

Data are expressed as mean ± standard deviation.

†Differences between groups evaluated with t-test.

‡Comparison between all groups assessed using analysis of variance.

The p-values in bold are statistically significant (p≤ 0.05).

FIG. 4

Table 3. Diagnostic accuracy of serum biomarkers in differentiating NAFL from NASH

| Biomarker | AUROC | 95% CI | p-value* |
|---|---|---|---|
| PGE2 | 0.81 | 0.60 – 1.00 | 0.0043 |
| dhk PGD2 | 0.93 | 0.82 – 1.00 | <0.0001 |
| Tetranor 12-HETE | 0.81 | 0.59 – 1.00 | 0.0077 |
| 15-HETE | 0.91 | 0.76 – 1.00 | <0.0001 |
| 11,12-diHETrE | 1.00 | --- | --- |
| 14,15-diHETrE | 0.82 | 0.62 – 1.00 | 0.0022 |
| 20-COOH AA | 0.96 | 0.86 – 1.00 | <0.0001 |
| 9-oxoODE | 0.73 | 0.48 – 0.99 | 0.0732 |
| 12,13 EpOME | 0.87 | 0.68 – 1.00 | 0.0001 |
| Panel | | | |
|    dhk PGD2 + 20-COOH AA | 1.00 | --- | --- |

FIG. 5

DIFFERENTIAL DIAGNOSIS OF LIVER DISEASE

RELATED APPLICATION DATA

This application is a U.S. National Stage Application filed under 35 U.S.C. § 371 and claims priority to International Application No. PCT/US2014/069389, filed Dec. 9, 2014, which application claims the benefit of priority under 35 U.S.C. § 119(e) of the U.S. Patent Application No. 61/914,345, filed on Dec. 10, 2013, the entire contents of which are incorporated herein by reference.

GRANT INFORMATION

This invention was made with government support under DK090303 and GM069338 awarded by the National Institutes of Health. The government has certain rights in the invention.

FIELD OF THE INVENTION

The invention relates generally to the diagnosis of liver disease and specifically differentiating between nonalcoholic fatty liver, nonalcoholic steatohepatitis, and normal controls.

BACKGROUND INFORMATION

Nonalcoholic fatty liver disease (NAFLD) is the most common cause of chronic liver disease in the United States. It can be broadly sub-classified into nonalcoholic fatty liver (NAFL), which is thought to have minimal risk of progression to cirrhosis, and nonalcoholic steatohepatitis (NASH), which is thought to have an increased risk of progression to cirrhosis. The current diagnostic gold standard for differentiating whether a patient with NAFLD has NAFL versus NASH is liver biopsy. However, liver biopsy is an invasive procedure, which is limited by sampling variability, cost, and may be complicated by morbidity and rarely even death.

Accurate, non-invasive, biomarkers for the detection of NASH are currently not available. Substantially non-invasive (e.g., except for a blood draw) diagnosis of NASH is a major unmet medical need.

Previous studies have shown that lipotoxicity plays an important role in the pathogenesis of NASH. Recent data suggest that oxidized low density lipoprotein (oxLDL) as well as other lipid moieties have been implicated as increased in patients with NASH compared to those with NAFL.

Oxidized polyunsaturated fatty acids (PUFAs) and their metabolites are implicated in a wide range of inflammatory diseases and auto-oxidized linoleic and linolenic acids have been reported in NAFLD. With the recent evolution of liquid chromatographic-mass spectrometric based lipidomics techniques, a robust and comprehensive approach to the lipidomics analysis of hundreds of fatty acids, acylethanolamines and inflammatory eicosanoids, including their numerous metabolites arising from an array of cyclooxygenases, lipoxygenases, cytochrome P450s and non-enzymatic oxidations producing isoprostanes, as well as combinations thereof has been developed. Particular attention has been focused on the eicosanoids and related oxygenated metabolites derived from arachidonic acid (AA) and other PUFAs. Over 150 such metabolites can now be routinely quantified.

Patients diagnosed with NASH have an increased risk of developing cirrhosis. There is currently no cure for cirrhosis and patients are limited to treatments which can delay the progress of the disease, minimize damage to liver cells and reduce complications. Early diagnosis of NASH can halt progression of the disease and prevent progression to cirrhosis. However, the only method currently available to reliably diagnose NASH is liver biopsy, a very invasive procedure.

SUMMARY OF THE INVENTION

The present invention relates to the substantially non-invasive diagnosis of liver disease. This invention further relates to the use of plasma biomarkers to differentiate nonalcoholic steatohepatitis (NASH) from nonalcoholic fatty liver (NAFL) and non-nonalcoholic fatty liver disease (NAFLD), and normal controls. Specifically, the invention relates to the use of free eicosanoids and other polyunsaturated fatty acid (PUFA) metabolite levels in plasma to differentiate NASH from NAFL and non-NAFLD normal controls.

As discussed herein, profiling of plasma eicosanoids and other oxidized PUFA according to the invention can differentiate between patients with NASH versus NAFL versus uniquely phenotyped normal controls (e.g., with documented liver fat content of less than 5% by proton-density-fat-fraction (MRI-PDFF) by a magnetic resonance imaging (MRI)-based determination).

In one embodiment, the invention provides a method of predicting or assessing the risk of progression of liver disease in a patient diagnosed with liver disease. The method is practiced by determining the identity and quantity of one or more free eicosanoids and/or polyunsaturated fatty acid (PUFA) metabolites in lipid extracts obtained from a sample of plasma from the patient. An increase or a decrease in one or more free eicosanoids and/or PUFA metabolites compared to a suitable control as further described herein is indicative of an increased risk of progression of the liver disease, for which therapy can be adjusted accordingly.

Preferably, the one or more free eicosanoids and/or PUFA metabolites is measured in a plasma sample from the patient, from which lipids containing the target molecules have been extracted. The identity and quantity of the eicosanoids and/or PUFA metabolites are determined and compared to their levels in normal controls.

In one aspect of this embodiment, the nonalcoholic liver disease (NAFLD) is a nonalcoholic fatty liver (NAFL). In another aspect, the NAFLD is nonalcoholic steatohepatitis (NASH). In a further aspect, the risk of progression of liver disease is progression to cirrhosis.

In a further aspect, the one or more free eicosanoids and/or PUFA metabolites are selected from the group consisting of PGE2, dhk PGD2, tetranor 12-HETE, 15-HETE, 11,12-diHETrE, 14,15-diHETrE, 20-COOH AA, 9-oxoODE, 12,13 EpOME, or any combination thereof. In a specific aspect, the one or more free eicosanoids and/or PUFA metabolites is 11,12-diHETrE, dhk PGD2 and/or 20-COOH AA, or any combination thereof. In a preferred aspect, the one or more free eicosanoids and/or PUFA metabolites is dhk PGD2 and 20-COOH AA. In another preferred aspect, the one free eicosanoid is 20-COOH AA.

In an additional aspect, the one or more free eicosanoids and/or PUFA metabolites is measured by AUROC. In a further aspect, the AUROC is about at least 0.8. In another aspect, the AUROC is about at least 0.9. In still another aspect, the AUROC is about at least 0.99.

In an additional embodiment, the present invention provides a method of distinguishing nonalcoholic steatohepatitis (NASH) from nonalcoholic fatty liver in a patient diagnosed with liver disease. The method is practiced by determining the identity and quantity of one or more free eicosanoids and/or polyunsaturated fatty acid (PUFA) metabolites in lipid extracts obtained from a sample of plasma from the patient.

Again, the one or more free eicosanoids and/or PUFA metabolites are preferably measured in a plasma sample from the patient, from which lipids containing the target molecules have been extracted, though it is possible that the determination can be carried out on a non-lipid extracted plasma sample. The identity and quantity of the eicosanoids and/or PUFA metabolites are determined and compared to their levels in normal controls. A statistically significant increase or decrease in the levels of the one or more free eicosanoids and/or PUFA metabolites compared to normal controls and, for differentiation, those obtained from non-alcoholic fatty liver and non-nonalcoholic fatty liver disease indicates that the patient has NASH. Therapy can then be applied accordingly.

In an aspect, the one or more free eicosanoids and/or PUFA metabolites is selected from the group consisting of PGE2, dhk PGD2, tetranor 12-HETE, 15-HETE, 11,12-diHETrE, 14,15-diHETrE, 20-COOH AA, 9-oxoODE, 12,13 EpOME, or any combination thereof. In a specific aspect, the one or more free eicosanoids and/or PUFA metabolites is 11,12-diHETrE, dhk PGD2 and/or 20-COOH AA, or any combination thereof. In a preferred aspect, the one or more free eicosanoids and/or PUFA metabolites is dhk PGD2 and 20-COOH AA.

In an additional aspect, the one or more free eicosanoids and/or PUFA metabolites is measured by AUROC. In a further aspect, the AUROC is about at least 0.8. In another aspect, the AUROC is about at least 0.9. In still another aspect, the AUROC is at least 0.99.

In a further embodiment, the present invention provides a method of distinguishing nonalcoholic steatohepatitis (NASH) from nonalcoholic fatty liver and non-nonalcoholic fatty liver disease comprising measuring the level of one or more free eicosanoids and/or polyunsaturated fatty acid (PUFA) metabolites in lipids extracted from a plasma sample from the patient. An increase in the levels of the one or more free eicosanoids and/or PUFA metabolites compared to normal controls and, for differentiation, those obtained in nonalcoholic fatty liver and non-nonalcoholic fatty liver disease indicates that the patient has NASH. Therapy can therefore be applied accordingly.

In an aspect, the one or more free eicosanoids and/or PUFA metabolites is selected from the group consisting of PGE2, dhk PGD2, tetranor 12-HETE, 15-HETE, 11,12-diHETrE, 14,15-diHETrE, 20-COOH AA, 9-oxoODE, and 12,13 EpOME, or any combination thereof. In a specific aspect, the one or more free eicosanoids and/or PUFA metabolites is 11,12-diHETrE, dhk PGD2 and/or 20-COOH AA. In a preferred aspect, the one or more free eicosanoids and/or PUFA metabolites is dhk PGD2 and 20-COOH AA.

In an additional aspect, the one or more free eicosanoids and/or PUFA metabolites is measured by AUROC. In a further aspect, the AUROC is about at least 0.8. In another aspect, the AUROC is about at least 0.9.

Advantageously, the method of the invention enables physicians to potentially intervene at an earlier stage of liver disease than previously possible by leveraging a non-invasive and accurate test for the progression of such disease.

BRIEF DESCRIPTION OF THE DRAWINGS

FIG. 3 (Table 1) shows the baseline demographic, clinical, biochemical, and histological characteristics of the patients in the study population.

FIG. 4 (Table 2) shows eicosanoid metabolites in normal controls versus non-alcoholic fatty liver disease versus non-alcoholic steatohepatitis.

FIG. 5 (Table 3) shows the diagnostic accuracy of serum biomarkers differentiating NAFL from NASH.

DETAILED DESCRIPTION OF THE INVENTION

Figure 1:
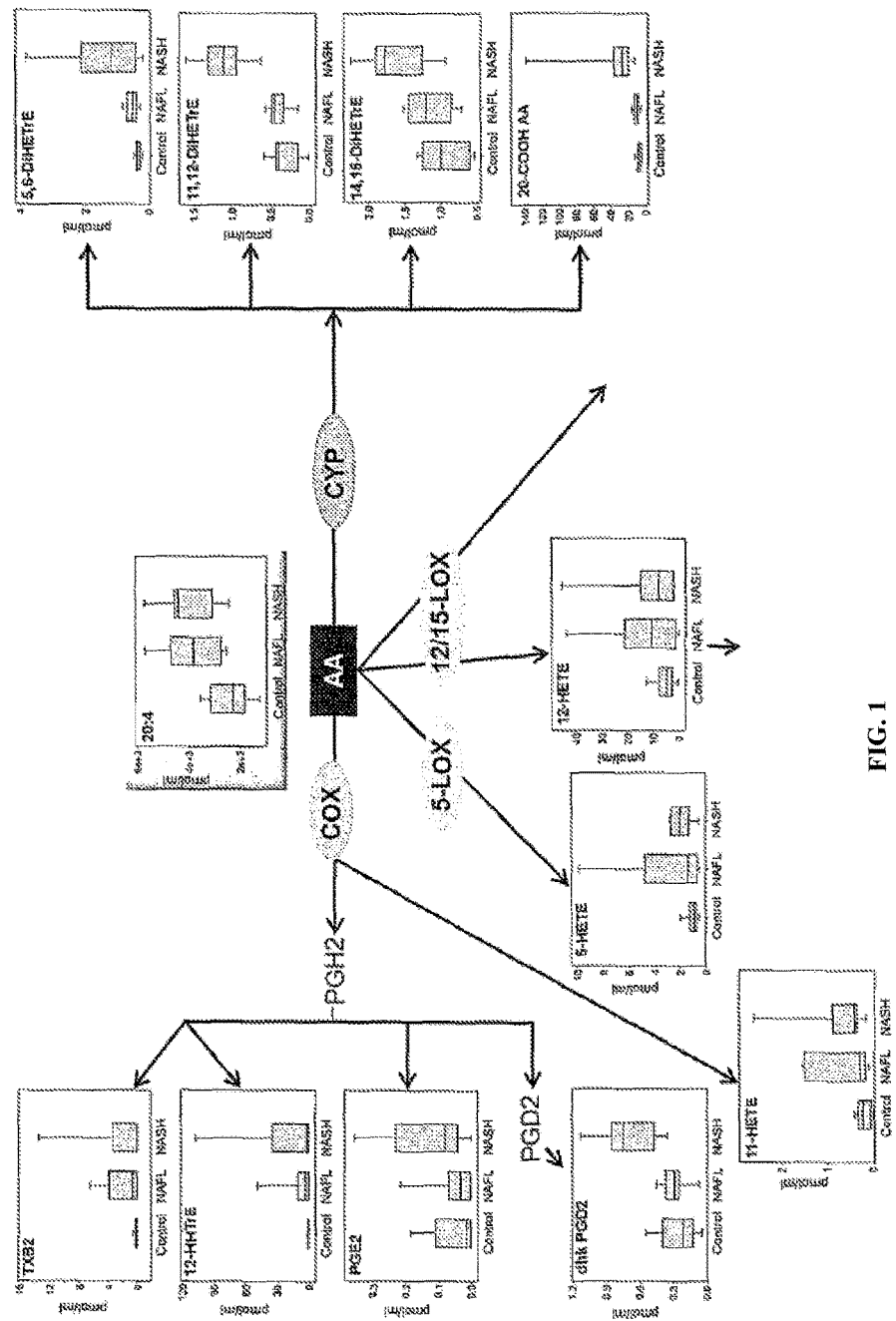
FIG. 1 shows arachidonic acid derived metabolites. The quantitative amounts of plasma free arachidonic acid (AA) and its metabolites derived from cyclooxygenase (COX), 5-lipoxygenase (5-LOX), 12- and 15-lipoxygenase (12/15-LOX) and cytochrome P450 (CYP) activities are shown in the three clinical arms for each metabolite. The results are displayed as Box-and-Whisker plots with the lower boundary of the box indicating the 25th percentile, the line within the box indicating the median and the upper boundary of the box indicating the 75th percentile. The whiskers indicate the lower and upper extremes of the data range.

The present invention relates to the diagnosis of liver disease. This invention further relates to the use of plasma biomarkers to differentiate nonalcoholic steatohepatitis (NASH) from nonalcoholic fatty liver (NAFL) and normal controls without non-nonalcoholic fatty liver disease (NAFLD). Specifically, the invention relates to the use of free eicosanoids and other polyunsaturated fatty acid (PUFA) metabolite levels in plasma to differentiate NASH from NAFL and non-NAFLD normal controls.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The definitions set forth below are for understanding of the disclosure but shall in no way be considered to supplant the understanding of the terms held by those of ordinary skill in the art.

Liver Disease

Liver disease is a type of damage to or disease of the liver. There are more than a hundred kinds of liver disease. The most widely spread are as follows: Fascioliasis; Hepatitis; Alcoholic liver disease; Fatty liver disease; Cirrhosis; liver; biliary; sclerosing cholangitis; Centrilobular necrosis; Budd-Chiari syndrome; Hereditary liver diseases (hemochromatosis, involving accumulation of iron in the body, and Wilson's disease); transthyretin-related hereditary amyloidosis; and Gilbert's syndrome.

As used herein, the term "liver disease" refers to any disease or disorder that affects the liver. Examples of liver disease include, but are not limited to, Alagille Syndrome; Alcohol-Related Liver Disease; Alpha-1 Antitrypsin Deficiency; Autoimmune Hepatitis; Benign Liver Tumors; Biliary Atresia; Cirrhosis; Galactosemia; Gilbert Syndrome; Hemochromatosis; Hepatitis A; Hepatitis B; Hepatitis C; Hepatocellular Carcinoma; Hepatic Encephalopathy; Liver Cysts; Liver Cancer; Newborn Jaundice; Non-Alcoholic Fatty Liver Disease (including nonalcoholic fatty liver and nonalcoholic steatohepatitis); Primary Biliary Cirrhosis (PBC); Primary Sclerosing Cholangitis (PSC); Reye Syndrome; Type I Glycogen Storage Disease and Wilson Disease.

Nonalcoholic Fatty Liver Disease

Non-alcoholic fatty liver disease (NAFLD) is one cause of a fatty liver, occurring when fat is deposited in the liver not due to excessive alcohol use. NAFLD is related to insulin resistance and the metabolic syndrome and may respond to treatments originally developed for other insulin-resistant states (e.g. diabetes mellitus type 2) such as weight loss, metformin and thiazolidinediones. NAFLD can be sub-classified as non-alcoholic steatohepatitis (NASH) and nonalcoholic fatty liver (NAFL). NASH is the more extreme form of NAFLD, and is regarded as a major cause of cirrhosis of the liver of unknown cause.

Most patients with NAFLD have few or no symptoms. Patients may complain of fatigue, malaise, and dull right-upper-quadrant abdominal discomfort. Mild jaundice may be noticed although this is rare. More commonly NAFLD is diagnosed following abnormal liver function tests during routine blood tests. NAFLD is associated with insulin resistance and metabolic syndrome (obesity, combined hyperlipidemia, diabetes mellitus (type II) and high blood pressure).

Common findings are elevated liver enzymes and a liver ultrasound showing steatosis. An ultrasound may also be used to exclude gallstone problems (cholelithiasis). A liver biopsy (tissue examination) is the only test widely accepted as definitively distinguishing NASH from other forms of liver disease and can be used to assess the severity of the inflammation and resultant fibrosis.

Nonalcoholic Fatty Liver

Nonalcoholic fatty liver (NAFL) is a type of NAFLD and is a condition in which fat accumulates in the liver cells. NAFL has minimal risk of progressing to cirrhosis. Simple fatty liver usually does not damage the liver, but is a condition that can be identified by liver biopsy. Simple fatty liver is not associated with any other liver abnormalities such as scarring or inflammation. It is a common finding in patients who are very overweight or have diabetes mellitus. A patient has a fatty liver when the fat makes up at least 5% of the liver.

Nonalcoholic Steatohepatitis

Nonalcoholic steatohepatitis (NASH) is a common, often "silent" liver disease. The major feature in NASH is fat in the liver, along with inflammation and damage. Most people with NASH feel well and are not aware that they have a liver problem. Nevertheless, NASH can be severe and can lead to cirrhosis, in which the liver is permanently damaged and scarred and no longer able to work properly.

NASH is usually first suspected in a person who is found to have elevations in liver tests that are included in routine blood test panels, such as alanine aminotransferase (ALT) or aspartate aminotransferase (AST). When further evaluation shows no apparent reason for liver disease and when x rays or imaging studies of the liver show fat, NASH is suspected. The only means of providing a definitive diagnosis of NASH and separating it from simple fatty liver is a liver biopsy. NASH is diagnosed when fat along with inflammation and damage to liver cells is observed from the biopsy. If the tissue shows fat without inflammation and damage, NAFL or NAFLD is diagnosed. Currently, no blood tests or scans can reliably provide this information.

Eicosanoids

Eicosanoids are signaling molecules made by oxidation of 20-carbon fatty acids, such as arachidonic acid or other polyunsaturated fatty acids (PUFAs). They exert complex control over many bodily systems; mainly in growth during and after physical activity, inflammation or immunity after the intake of toxic compounds and pathogens, and as messengers in the central nervous system. Eicosanoids include the prostaglandins, prostacyclin, thromboxane, leukotrienes and other metabolites formed by enzymatic or non-enzymatic addition of oxygen to PUFAs.

Eicosanoids are derived from either omega-3 ($\omega$-3) or omega-6 ($\omega$-6) fatty acids. In general, the $\omega$-6 eicosanoids are pro-inflammatory; $\omega$-3s are much less so or may even be anti-inflammatory. The amounts and balance of these fats in a person's diet will affect the body's eicosanoid-controlled functions, with effects on cardiovascular disease, triglycerides, blood pressure, and arthritis. Anti-inflammatory drugs such as aspirin and other NSAIDs act by downregulating eicosanoid synthesis.

There are multiple subfamilies of eicosanoids, including the prostaglandin, e.g. prostacyclins, thromboxanes, lipoxins, and leukotrienes. For each, there are two or three separate series, derived from either a $\omega$-3 or an $\omega$-6 EFA. These series' different activities largely explain the health effects of $\omega$-3 and $\omega$-6 fats.

Polyunsaturated Fatty Acid

Polyunsaturated fatty acids (PUFAs) are fatty acids that contain more than one double bond in their backbone. This class includes many important compounds, such as essential fatty acids. Polyunsaturated fatty acids can be classified in various groups by their chemical structure: methylene-interrupted polyenes, conjugated fatty acids and other PUFAs. PUFAs include other fatty acids than those containing 20 carbons (eicosa) such as 18 carbon containing linoleic acid and linolenic acid and 22 carbon containing decosapentenoic acid (DPA) and docosahexenoic acid (DHA) but also metabolites of arachidonic acid and other 20 carbon fatty acids such as eicosatrienoic acid (ETA) and eicosapentenoic acid (EPA) derived from cyclooxygenases, lipoxygenases, cytochrome P450s and non-enzymatic oxidations. Examples of enzymes which act on arachidonic acid and other PUFAs to produce PUFAs include, as is known, COX, 5-LOX, 12/15-LOX and CYP. PUFAs can also undergo non-enzymatic oxidation.

Examples of free eicosanoids and PUFA metabolites include, but are not limited to, PGE2 (prostaglandin E2), dhk PGD2 (13,14-dihydro-15-keto prostaglandin D2), tetranor 12-HETE (2,3,4,5-tetranor 12(R)-HETE), 15-HETE (15-HydroxyY-5Z,8Z,11Z,13E-eicosatetraenoic acid), 11,12-diHETrE (11,12-dihydroxy-eicosatrienoic acid), 14,15-diHETrE (14,15-Dihydroxy-5,8,11-icosatrienoic acid), 20-COOH AA (20-carboxy arachidonic acid), 9-oxoODE (9-oxo-octadecadienoic acid), 12,13 EpOME (12(13)-isoleukotoxin), TxB2 (thromboxane B2), 12-HHTrE (12-hydroxy-hepta-decatrienoic acid), 11-HETE (11-hydroxy-5Z,8Z,12E,14Z-eicosatetraenoic acid), 5-HETE (5-hydroxy-6E-8Z,11Z,14Z-eicosatetraenoic acid), 5,6-diHETrE (5,6-dihydroxy-8Z,11Z,14Z-eicosatrienoic acid), 14,15-diHETrE (14,15-Dihydroxy-5,8,11-icosatrienoic acid), 13-HODE (13-Hydroxyoctadecadienoic acid;), 9-HODE (9-Hydroxyoctadecadienoic acid;), 9,10 EpOMe, 9,10 diHOME (the diol resulting from the soluble epoxide hydrolase opening of (±)12,13-EpOME), 12,13 diHOME, 9-HOTrE, 15-HETrE (15S-hydroxy-8Z,11Z,13E-eicosatrienoic acid), 12-HEPE (12-Hydroxy-5,8,10,14,17-icosapentaenoic acid), 14 HDoHE (14-hydroxy docosahexaenoic acid), 16 HDoHE (16-hydroxy docosahexaenoic acid) and 19,20 DiHDPA (19,20-dihydroxy-4Z,7Z,10Z,13Z,16Z docosapentaenoic acid), plasma free linoleic acid (LA), α-linolenic acid (ALA), eicosatrienoic acid (ETA), eicosapentaenoic acid (EPA) and docosahexaenoic acid (DHA) and their metabolites derived from 5-LOX, 12/15-LOX and CYP.

The present invention also provides a method of predicting or assessing the risk of progression of liver disease in a patient diagnosed with liver disease comprising measuring the level of one or more free eicosanoids and/or polyunsaturated fatty acid (PUFA) metabolites in the plasma of the patient wherein an increase in free eicosanoids and/or PUFA metabolites or a decrease in one or more specific ones due to conversion, which could include oxidation, to a different eicosanoid or PUFA is indicative of an increased risk of progression of the liver disease. In one aspect, the nonalcoholic fatty liver disease (NAFLD) is a nonalcoholic fatty liver (NAFL). In another aspect, the NAFLD is nonalcoholic steatohepatitis (NASH).

In a particularly useful aspect, it is shown herein that plasma eicosanoid profiling can differentiate between NAFL and NASH. As described below in the examples, several eicosanoid moieties were identified that were significantly different between normal versus NAFL versus NASH, 11,12-diHETrE, dkPGD2 and 20-COON AA were greatly elevated in NASH patients versus NAFL versus normal controls in a dose-dependent manner. This data provides evidence that 11,12-diHETrE, dkPGD2 and 20-COON AA are the leading eicosanoid candidate biomarkers for the non-invasive diagnosis of NASH.

Figure 2:
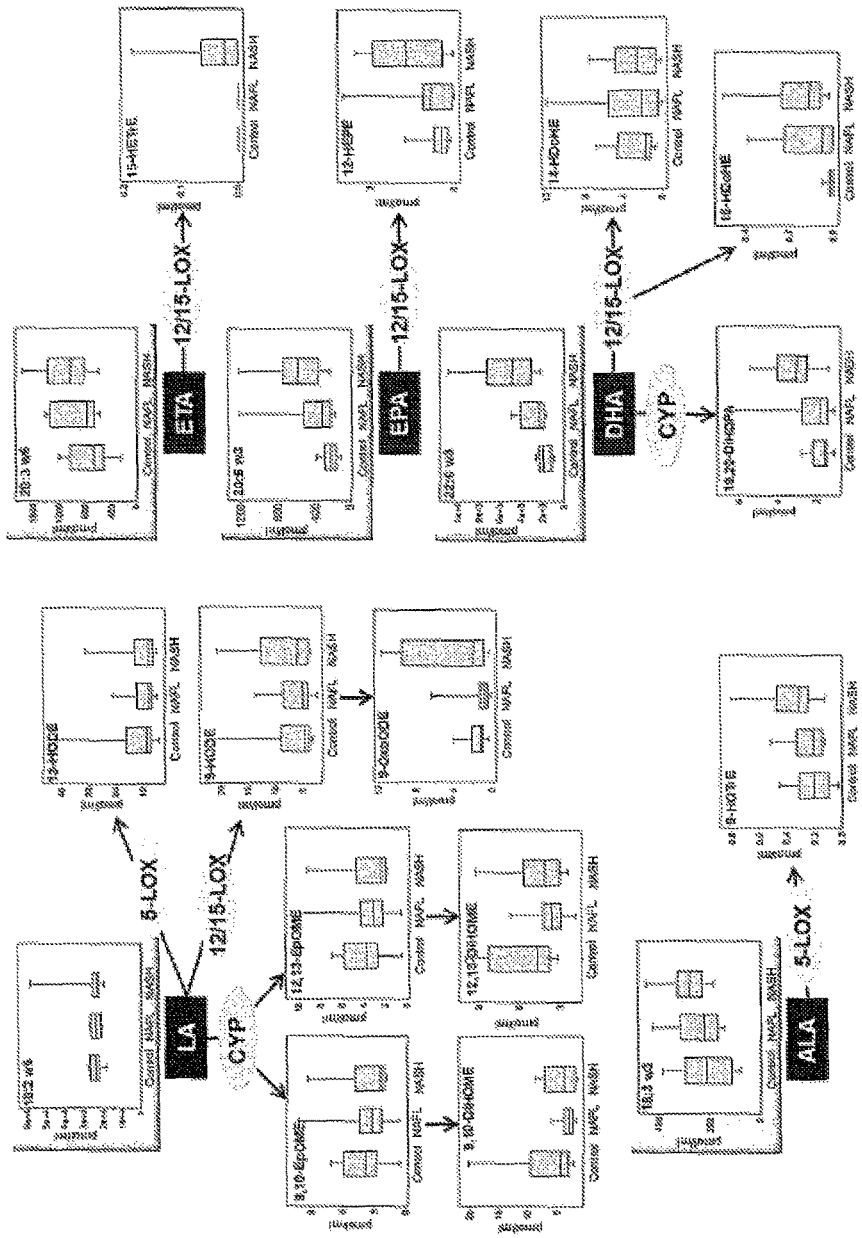
FIG. 2 shows alternative substrate derived metabolites. The quantitative amounts of plasma free linoleic acid (LA), α-linolenic acid (ALA), eicosatrienoic acid (ETA), eicosapentaenoic acid (EPA) and docosahexaenoic acid (DHA) and their metabolites derived from 5-LOX, 12/15-LOX and CYP activities are shown in the three clinical arms for each metabolite. The results are displayed as Box-and-Whisker plots with the lower boundary of the box indicating the $25^{th}$ percentile, the line within the box indicating the median and the upper boundary of the box indicating the $75^{th}$ percentile. The whiskers indicate the lower and upper extremes of the data range.

These results differ from previously reported results in that only metabolites that were present in their free form and without KOH treatment were measured. Even though the levels of the free eicosanoids are much lower than the eicosanoids esterified to lipids, this approach captures many more metabolites and allows for a much broader profiling strategy. It also avoids destruction of some eicosanoids and PUFAs by the treatment with bases or acids, which is an essential step in the analysis of eicosanoid esterified to lipids. In NAFLD, normal lipid metabolism is disrupted leading to increased levels of free fatty acids and triglyceride synthesis. Free fatty acids have been shown to elicit hepatotoxicity and may stimulate the progression from NAFL to NASH via several mechanisms. They can be directly cytotoxic and stimulate the production of inflammatory pathways in hepatocytes. These fatty acids also serve as precursors for inflammatory eicosanoids. Consistent with this, the plasma levels of several free PUFAs were consistently higher in NAFL and NASH compared with healthy controls (FIGS. 1 and 2).

However, there were no differences between NAFL and NASH suggesting that plasma free fatty acids are poor markers to differentiate between the various stages of NAFLD. By contrast, their conversion to eicosanoids may constitute a critical mechanism in disease progression and the analysis of eicosanoid levels, rather than fatty acid levels, may be a useful clinical tool to discriminate between NAFL and NASH.

The one or more free eicosanoids and/or PUFA metabolites may be selected from the group consisting of PGE2, dhk PGD2, tetranor 12-HETE, 15-HETE, 11,12-diHETrE, 14,15-diHETrE, 20-COOH AA, 9-oxoODE, 12,13 EpOME, or any combination thereof. In a specific aspect, the one or more free eicosanoids and/or PUFA metabolites is 11,12-diHETrE, dhk PGD2 and/or 20-COOH AA, or any combination thereof. In a preferred aspect, the one or more free eicosanoids and/or PUFA metabolites is dhk PGD2 and 20-COOH AA. In another preferred aspect, the one or more free eicosanoids and/or PUFA metabolites is 20-COOH AA.

The method is practiced by determining the level of one or more free eicosanoids and/or polyunsaturated fatty acid (PUFA) metabolites in a sample of the plasma of a patient. As used herein, the term "sample" refers to any biological sample from a patient. Examples include, but are not limited to, saliva, hair, skin, tissue, sputum, blood, plasma, serum, vitreal, cerebrospinal fluid, urine, sperm and cells.

Lipids are extracted from the plasma sample, as detailed further in the Examples. The identity and quantity of eicosanoids and/or PUFA metabolites in the extracted lipids is first determined and then compared to suitable controls. The determination may be made by any suitable lipid assay technique, preferably one which is high throughput; e.g., spectrophotometric analysis (such as the colorimetric sulfo-phospho-vanillin (SPV) assessment method of Cheng, et al., *Lipids*, 46(1):95-103 (2011)). Other analytical methods suitable for detection and quantification of lipid content will be known to those in the art including, without limitation, ELISA, NMR, UV-Vis or gas-liquid chromatography, HPLC, UPLC and/or MS or RIA methods enzymatic based chromogenic methods. Lipid extraction may also be performed by various methods known to the art, including the conventional method for liquid samples described in Bligh and Dyer, *Can J Biochem Physiol.*, 37, 911 (1959).

For general determination of the progression of liver disease, the values obtained may be compared to normal controls. For distinguishing nonalcoholic steatohepatitis (NASH) from nonalcoholic fatty liver (NAFL) in a patient diagnosed with having nonalcoholic liver disease (NAFLD); e.g., for determination of NASH or cirrhosis and/or, for differentiation of NASH and NAFL. The controls may include normal controls. An increase in free eicosanoids and/or PUFA metabolites compared to the controls is indicative of an increased risk of progression of the liver disease and/or the desired differentiation of NASH, for which therapy can be applied accordingly. In some cases, there may be a decrease in one or more eicosanoid and/or PUFA, if a normal metabolite is oxidized or converted to another metabolite.

Levels of free eicosanoids and PUFA metabolites are expressed as AUROC (Area under Receiver Operating Characteristic Curve). AUROC is determined by measuring levels of free eicosanoids and PUFA metabolites by stable isotope dilution. Briefly, identical amounts of deuterated internal standards are added to each sample and to all the primary standards used to generate standard curves. Levels of eicosanoids and PUFA metabolites are calculated by determining the ratios between endogenous metabolite and matching deuterated internal standards. Ratios are converted to absolute amounts by linear regression. Individual eicosanoid metabolites are assessed for diagnostic test performances and capability to differentiating between NAFL and NASH using statistical analyses including chi-square test, t-test and AUROC.

An increased risk of progression of liver disease is determine by AUROC values about at least 0.8, about at least 0.9, about at least 0.95, about at least 0.96, about at least 0.97, about at least 0.98, about at least 0.99 or 1.0.

The invention in all its aspects is illustrated further in the following Examples. The Examples do not, however, limit the scope of the invention, which is defined by the appended claims.

EXAMPLE 1

Cohort Demographics

This study included 19 patients with NAFLD (10 NAFL cases and 9 cases of NASH), and 10 non-NAFLD normal controls. The detailed baseline characteristics including demographics, body-mass-index, biochemical tests, lipid profile, MRI-PDFF for controls and liver biopsy data on patients with NAFLD is described in Table 1. Non-NAFLD controls were younger, had lower BMI, and had a lower serum ALT, AST, GGT, and glucose and insulin levels as expected. Routine liver related and metabolic tests did not significantly differ between NAFL versus NASH (Table 1) except plasma triglyceride were marginally higher in patients with NASH. Compared to patients with NAFL, patients with NASH had more severe liver histology with higher degree of steatosis, ballooning degeneration, lobular inflammation and fibrosis.

EXAMPLE 2

PUFA and Metabolite Lipidomics Profiling

At present, there are no noninvasive biomarkers with sufficient specificity to distinguish NASH from other fatty liver states. Liver biopsy remains the benchmark to reliably identify NAFL and NASH but the procedure is invasive and carries certain risks. Thus, there is great demand from the clinical community for the development of noninvasive procedures capable of accurately characterizing and staging NAFLD, as that furnishes valuable information on treatment options and prognosis. Inflammation and oxidative stress contribute to disease progression from steatosis with relatively benign outcome to NASH with risk of cirrhosis and hepatocellular carcinoma. Here, liquid chromatography and mass spectrometry were used to profile and quantitate bioactive lipids and lipid peroxidation products in circulation that are characteristic of hepatic inflammation in NASH patients.

Complete eicosanoid profiles were established and assessed the plasma levels of free eicosanoids derived from arachidonic acid (20:4 ω6) and related polyunsaturated fatty acids (PUFAs) including linoleic acid (18:2 ω6), a-linolenic acid (18:3 ω3), dihomo-gamma-linolenic acid (20:3 ω6), eicosapentaenoic acid (20:5 ω3) and docosahexaenoic acid (22:6 ω3) in well-characterized cohorts of patients with suspected NAFL or NASH, stratified according to their liver biopsy scores (Table 1). The initial eicosanoid profile consisted of 158 individual metabolites that our analytical platform can reliably measure. Of these, 26 eicosanoids were present at measurable levels in the control, NAFL or NASH plasma samples (Table 2). These mediators are generated through complex biosynthetic mechanisms and multiple routes for modification and degradation (27). As shown in FIGS. 1 and 2, eicosanoids derived from all three major enzymatic pathways, the cyclooxygenase pathway (COX-1 and COX-2), the lipoxygenase pathway (5-LOX, 12-LOX and 15-LOX) and the cytochrome P450 (CYP) pathway were present at various amounts in the control, NAFL and NASH samples. COX-derived thromboxane B2 ($TXB_2$) and 12-hydroxy-heptatrienoic acid (12 HHTrE), one of the primary AA metabolites produced by thromboxane synthase in human platelets were detected at low levels in the control samples but were significantly higher in both the NAFL and NASH samples; however, no significant difference was found between NAFL and NASH. In contrast, prostaglandin $E_2$ ($PGE_2$) was elevated only in the NASH samples and no differences were observed between the controls and NAFL (FIG. 1). Prostaglandin $D_2$ ($PGD_2$) was not detected in any of the samples but the degradation product 13,14-dihydro-15-keto $PGD_2$ (dhk $PGD_2$) was significantly higher in NASH compared with NAFL (p-value<0.0011) or control (p-value<0.0002) (FIG. 1).

LOX-derived metabolites were also increased in NAFLD. Of note, while the AA-derived products of 5-LOX, 12/15 LOX pathways appear to be highest in NAFL (FIG. 1), the metabolites from related PUFAS including linoleic acid, a-linolenic acid, dihomo-gamma-linolenic acid, EPA and DHA were generally higher in NASH (FIG. 2). Similarly, the AA-derived metabolites of the CYP pathway were predominantly elevated in NASH but unchanged in NAFL compared with healthy controls (FIGS. 1 and 2). In particular, 11,12-dihydroxy-eicosatrienoic acid (11,12-diHETrE) and 14,15-dihydroxy-eicosatrienoic acid (14,15-diHETrE) were significantly elevated in NASH compared to NAFL or controls. These metabolites are produced by the action of soluble epoxide hydrolase (sEH) on epoxyeicosatrienoic acids, which are the primary products of the epoxygenase pathway of CYP on the initial substrate AA. A number of biological effects have been ascribed to epoxyeicosatrienoic acids including cardioprotective vasodilation, leukocyte anti-migratory and anti-inflammatory actions. Conversion of the epoxides to their corresponding diols by the sEH decreases their functional levels and thereby diminishes the associated health benefits. Similarly, 20-hydroxyeicosatetraenoic acid (20-HETE), an AA metabolite synthesized by the CYP hydroxylase pathway, is reported to have important vasoactive properties. 20-HETE was not detected in plasma, but a consistent increase of 20-carboxy arachidonic acid (20-COON AA) was found in NASH samples, but it did not reach statistical significance in this particular sample set when comparing NAFL vs NASH (Table 2). The conversion of 20-HETE to 20-COON AA is catalyzed by CYP enzymes and is responsible for reduced bioactivity.

EXAMPLE 3

Identification of a Panel of Eicosanoids as a Diagnostic Tool for Detecting NASH Based upon Table 2, nine biomarkers were found to be significant in the assessment of NAFLD. Their individual diagnostic test performances were assessed using AUROC and reported them in Table 3. The top candidate as a single biomarker for differentiating NAFL from NASH was 11,12s diHETrE with an AUROC of 1. In addition, a panel including dkPGD2 and 20-COON AA was found that demonstrated an AUROC of 1.

EXAMPLE 4

Methods

Study design and participants. This study was a cross-sectional analysis derived from a prospective nested case-control study including three groups of uniquely phenotyped patients with biopsy-proven NAFLD (including NASH and NAFL) and normal non-NAFLD controls. All participants were derived from the UCSD NAFLD Research Clinic and were seen between January 2011 and November 2012(18-20). All participants provided a written informed consent and underwent a detailed standardized clinical research visit including medical history, alcohol use and quantification history (using Audit and Skinner questionnaire), physical examination, anthropometrics, fasting biochemical tests, as well as detailed exclusion of other causes of liver disease (please see inclusion and exclusion criteria below). A fasting plasma sample was collected in the morning of the clinical research visit and stored in a −80° C. freezer housed in the UCSD NAFLD Translational Research Unit.

Description of cohort. All cases of NAFLD included in this study had a liver biopsy-confirmed diagnosis of NAFLD. Biopsy was scored by an experienced liver pathologist who was blinded to clinical data, lipidomic and imaging data. The NASH CRN histologic scoring system was used to score biopsies. NAFLD activity score (NAS) as well as fibrosis scores were recorded in all patients. NAS score ranges from 0-8 and is the summation of the degree of steatosis (0-3), lobular inflammation (0-3), and hepatocellular ballooning (0-2). Liver fibrosis ranges from 0 to 4 with 0 being no fibrosis and 4 is cirrhosis.

Definition of NASH. Patients with biopsy-confirmed NAFLD who had predominantly zone-3 macrovesicular steatosis and lobular inflammation and the presence of classic ballooning degeneration were classified as having NASH.

Inclusion and Exclusion Criteria for the NAFLD. Inclusion criteria included age at least 18 years during the consent process, ability and willingness to give written, informed consent, minimal or no alcohol use history consistent with NAFLD (see exclusion criteria), and collection of plasma within 90 days of the liver biopsy. Exclusion criteria included clinical or histological evidence of alcoholic liver disease: Regular and excessive use of alcohol within the 2 years prior to interview defined as alcohol intake greater than 14 drinks per week in a man or greater than 7 drinks per week in a woman. Approximately 10 g of alcohol equals one 'drink' unit. One unit equals 1 ounce of distilled spirits, one 12-oz beer, or one 4-oz glass of wine, secondary causes of hepatic steatosis including previous surgeries, bariatric surgery, total parenteral nutrition, short bowel syndrome, steatogenic medications, evidence of chronic hepatitis B as marked by the presence of HBsAg in serum, evidence of chronic hepatitis C as marked by the presence of anti-HCV or HCV RNA in serum, evidence of other causes of liver disease, such as alpha-1-antitrypsin deficiency, Wilson's disease, glycogen storage disease, dysbetalipoproteinemia, known phenotypic hemochromatosis, autoimmune liver disease, or drug-induced liver injury, or concomitant severe underlying systemic illness that in the opinion of the investigator would interfere with the study.

Definition of normal controls. Novel aspect of this study was inclusion of a uniquely well-characterized non-NAFLD normal control group. Participants were classified as normal non-NAFLD by accurate hepatic fat quantification by MRI-PDFF derived fat fraction of less than 5% (18, 20). Liver biopsy is unethical in normal individuals. Other non-invasive measures such as ultrasound and computed tomography are inaccurate, and lack sensitivity especially at liver fat fraction between 1-10%. Therefore, MRI-PDFF was utilized in this study for accurate diagnosis of absence of hepatic steatosis (Noureddin et al. Hepatology (2013), 58:1930). MRI-PDFF is highly accurate, sensitive, reproducible, and precise.

Inclusion and Exclusion Criteria for Normal (non-NAFLD) control cohort. Inclusion criteria in the healthy (non-NAFLD) control group included (1) age greater than 18 years; (2) liver MRI-PDFF<5%; and (3) no history of known liver disease. Exclusion criteria included (1) age less than 18 years; (2) significant systemic illness; (3) inability to undergo MRI; and (4) evidence of possible liver disease, including any previous liver biopsy, positive hepatitis B surface antigen, hepatitis C viral RNA, or autoimmune serologies, alpha-1 antitrypsin deficiency, hemochromatosis genetic testing, or low ceruloplasmin.

Lipid extraction. Plasma samples for lipidomic profiling were obtained within 90 days of the liver biopsy and MRI-PDFF for cases and controls, respectively. All plasma samples were stored at −80° C., thawed once and immediately used for free fatty acid and eicosanoid isolation as described previously. Briefly, 50 µl plasma were spiked with a cocktail of 26 deuterated internal standards (individually purchased from Cayman Chemicals, Ann Arbor, Mich.) and brought to a volume of 1 ml with 10% methanol. The samples were then purified by solid phase extraction on Strata-X columns (Phenomenex, Torrance, Calif.), using an activation procedure consisting of consecutive washes with 3 ml of 100% methanol followed by 3 ml of water. The eicosanoids were then eluted with 1 ml of 100% methanol, the eluent was dried under vacuum and dissolved in 50 µl of buffer A consisting of 60/40/0.02 water/acetonitril/acetic acid=60/40/0.02 (v/v/v) and immediately used for analysis, as follows: For free fatty acids analysis, 50 µl of plasma were spiked with deuterated fatty acid standards and the free fatty acids were isolated by selective extraction with methanol and isooctane. The extracted fatty acids were derivatized and analyzed by gas chromatography and mass spectrometry, as described (Dumlao et al. (2011), 1811:724).

Reverse-phase liquid chromatography and mass spectrometry. Eicosanoids in plasma were analyzed and quantified by liquid chromatography tandem mass spectrometry (LC-MS/MS). Briefly, eicosanoids were separated by reverse phase chromatography using a 1.7 uM 2.1×100 mm BEH Shield Column (Waters, Milford, Mass.) and an Acquity UPLC system (Waters, Milford, Mass.). The column was equilibrated with buffer A and 5 µl of sample was injected via the autosampler. The samples were eluted with a step gradient starting with 100% Buffer A for 1 min, then to 50% buffer B (consisting of 50% acetonitril, 50 isopropanol and 0.02% acetic acid) over a period of 3 min and then to 100% buffer B over a period of 1 min. The liquid chromatography was interfaced with an IonDrive Turbo V ion source and mass spectral analysis was performed on a triple quadrupole AB SCIEX 6500 QTrap mass spectrometer (AB SCIEX, Framingham, Mass.). Eicosanoids were measured using electrospray ionization in negative ion mode and multiple reaction monitoring (MRM) using the most abundant and specific precursor ion/product ion transitions to build an acquisition method capable of detecting 158 analytes and 26 internal standards. The ionspray voltage was set at −4500 V at a temperature of 550° C. Collisional activation of the eicosanoid precursor ions was achieved with nitrogen as the collision gas with the declustering potential, entrance potential and collision energy optimized for each metabolite. Eicosanoids were identified by matching their MRM signal and chromatographic retention time with those of pure identical standards.

Quantitation of lipids. Eicosanoids and free fatty acids were quantitated by the stable isotope dilution method. Briefly, identical amounts of deuterated internal standards were added to each sample and to all the primary standards used to generate standard curves. To calculate the amount of eicosanoids and free fatty acids in a sample, ratios of peak areas between endogenous metabolite and matching deuterated internal standards were calculated. Ratios were converted to absolute amounts by linear regression analysis of standard curves generated under identical conditions.

Statistical analysis. The chi-square ($\times 2$) test was used for comparisons between categorical variables and the t-test was used for comparisons between continuous variables. We examined differences in the plasma eicosanoid profiles between normal controls, patients with biopsy-proven mild NAFL and patients with biopsy-proven NASH. Finally, we examined the diagnostic accuracy of nine biomarkers that yielded significant differences as a biomarker to differentiate NAFL from NASH. A two-tailed p-value 0.05 was considered statistically significant. Statistical analyses were performed using the SAS statistical software package version 9.4 (Cary, N.C., SAS Inc.).

What is claimed is:

1. A substantially non-invasive method of predicting or assessing the risk of progression of liver disease in a patient diagnosed with liver disease comprising:
   directly treating a plasma sample from a subject with alcohol to dissolve free eicosanoids and free polyunsaturated fatty acid (fPUFA) to obtain free-dissolved eicosanoids and free-dissolved fPUFAs;
   purifying the free-dissolved eicosanoids and free-dissolved fPUFAs;
   measuring the level of one or more free eicosanoids and/or PUFA metabolites selected from the group consisting of (i) dhk PGD2, (ii) 20-COOH AA, (iii) 11,12-diHETrE and dhk PGD2; (iv) 11,12-diHETrE and 20-COOH AA; (v) dhk PGD2 and 20-COOH AA and (vi) dhk PGD2, 20-COOH AA and 11,12-diHETrE, and
   determining the area under receiver operating characteristic curve (AUROC) based upon a ratio of the levels of the free-dissolved eicosanoids and/or free-dissolved fPUFA metabolites matched with deuterated internal standards of the same metabolite.

2. The method of claim 1, wherein the liver disease is a nonalcoholic fatty liver disease (NAFLD).

3. The method of claim 2, wherein the NAFLD is non-alcoholic steatohepatitis (NASH).

4. The method of claim 1, wherein the ratio or a converted absolute value amount is communicated to a physician.

5. The method of claim 1, wherein the one or more free eicosanoids and/or PUFA metabolites are dhk PGD2 and 20-COOH AA.

6. The method of claim 1, wherein the one or more free eicosanoids and/or PUFA metabolites is 20-COOH AA.

7. The method of claim 1, wherein the AUROC is about at least 0.8.

8. The method of claim 1, wherein the AUROC is about at least 0.9.

9. The method of claim 1, wherein the AUROC is about at least 0.99.

10. The method of claim 1, wherein the risk of progression of liver disease is progression to cirrhosis.

11. A substantially non-invasive method of distinguishing nonalcoholic steatohepatitis (NASH) from nonalcoholic fatty liver and non-nonalcoholic fatty liver disease (NAFLD) in a patient diagnosed with liver disease comprising:
   directly treating a plasma sample from a subject with alcohol to dissolve free eicosanoids and free polyunsaturated fatty acid (fPUFA) to obtain free-dissolved eicosanoids and free-dissolved fPUFAs;
   purifying the free-dissolved eicosanoids and free-dissolved fPUFAs;
   measuring the level of one or more free-dissolved eicosanoids and/or free-dissolved fPUFA metabolites selected from the group consisting of (i) dhk PGD2, (ii) 20-COOH AA, (iii) 11,12-diHETrE and dhk PGD2; (iv) 11,12-diHETrE and 20-COOH AA; (v) dhk PGD2 and 20-COOH AA and (vi) dhk PGD2, 20-COOH AA and 11,12-diHETrE; and
   determining the area under receiver operating characteristic curve (AUROC) based upon a ratio of the levels of the free-dissolved eicosanoids and/or free-dissolved fPUFA metabolites matched with deuterated internal standards of the same metabolite.

12. The method of claim 11, wherein the one or more free eicosanoids and/or PUFA metabolites is dhk PGD2 and 20-COOH AA.

13. The method of claim 11, wherein the one or more free eicosanoids and/or PUFA metabolites is 20-COOH AA.

14. The method of claim 11, wherein the AUROC is about at least 0.8.

15. The method of claim 11, wherein the AUROC is about at least 0.9.

16. The method of claim 11, wherein the AUROC is about at least 0.99.

17. A substantially non-invasive method of predicting or assessing the risk of progression of liver disease in a patient diagnosed with liver disease comprising
   (a) obtaining a sample comprising one or more free eicosanoids and/or free-polyunsaturated fatty acid (fPUFA) metabolites from the plasma of a patient;
   (b) spiking deuterated internal standards into each sample and primary standards used to generate a standard curve,
   (c) treating the sample with alcohol to dissolve free eicosanoids and free polyunsaturated fatty acid (fPUFA) to obtain free-dissolved eicosanoids and free-dissolved fPUFAs,
   (d) purifying the free-dissolved eicosanoids and free-dissolved fPUFAs;
   (e) measuring the level of one or more free-dissolved eicosanoids and/or free-dissolved fPUFA metabolites selected from the group consisting of (i) dhk PGD2, (ii) 20-COOH AA, (iii) 11,12-diHETrE and dhk PGD2; (iv) 11,12-diHETrE and 20-COOH AA; (v) dhk PGD2 and 20-COOH AA and (vi) dhk PGD2, 20-COOH AA and 11 ,12-diHETrE,
   (f) calculating the ratio between endogenous metabolite and matching deuterated internal standards;
   (g) converting the ratios to absolute amounts by linear regression; and
   (h) determining the area under receiver operating characteristic curve (AUROC) based upon the levels of the free-dissolved eicosanoids and/or free-dissolved fPUFA metabolites.

* * * * *